United States Patent [19]

Wirth et al.

[11] Patent Number: 4,761,495

[45] Date of Patent: Aug. 2, 1988

[54] METHOD RELATING TO PREPARATION OF ASPARTYL PEPTIDES

[75] Inventors: Didier Wirth, Paris; Dominique Gibert, Villers-sous-St. Leu; Annie Boutin, Villeneuve-La-Garenne, all of France

[73] Assignee: Isochem S.A., Gennevilliers, France

[21] Appl. No.: 690,682

[22] Filed: Jan. 11, 1985

[30] Foreign Application Priority Data

Jan. 19, 1984 [FR] France ................................ 84 00794

[51] Int. Cl.⁴ ..................... C07C 101/02; C07C 69/00; C07C 101/24; C07C 101/26
[52] U.S. Cl. ....................................... 560/41; 560/142; 560/144; 560/145; 560/169; 562/561; 562/565; 562/450
[58] Field of Search ................... 260/112.5 R, 998.21; 530/339; 560/41, 142, 144, 145, 169; 562/450, 561, 565

[56] References Cited

U.S. PATENT DOCUMENTS

| | | |
|---|---|---|
| 3,492,131 | 1/1970 | Schlatter . |
| 3,642,491 | 2/1972 | Schlatter . |
| 3,714,139 | 1/1973 | Schlatter et al. . |
| 3,780,189 | 12/1973 | Scott . |
| 3,800,046 | 3/1974 | Schlatter . |
| 3,830,792 | 8/1974 | Tilak . |
| 3,879,372 | 4/1975 | Boesten . |
| 3,962,207 | 6/1976 | Uchiyama et al. ............ 260/112.5 R |
| 4,332,718 | 6/1982 | Takahashi et al. . |
| 4,333,872 | 6/1982 | Sampathkumar et al. . |
| 4,343,741 | 8/1982 | Townsend et al. . |
| 4,517,119 | 5/1985 | Felix et al. ......................... 530/339 |

FOREIGN PATENT DOCUMENTS

| | | |
|---|---|---|
| 0035047 | 9/1981 | European Pat. Off. . |
| 0149582 | 7/1985 | European Pat. Off. . |
| 2558471 | 7/1985 | France . |
| 2571365 | 4/1986 | France . |

OTHER PUBLICATIONS

Hirshmann et al., *J. Am. Chem. Soc.*, 93, No. 11, 2746–2754, (1971).
*Chemical Abstracts*, 100, 624 (1984), abst. No. 192293a.
Bryant, J. Chem. Soc., 1959, p. 3868.
A. Balog, Rev. of Rumanian Chem., 15, p. 1375, (1970).
Wendlberger, Houben-Weyl, "Methoden der Organishe Chemie, 1512, p. 8, (1974).
Hirschmann, Ralph et al., JACS, 93, 2746, (1971).
Tetrahedron Letters, No. 7, pp. 613–616, Printed Great Britain, 1979.

*Primary Examiner*—J. R. Brown
*Assistant Examiner*—F. T. Moezie
*Attorney, Agent, or Firm*—Spencer & Frank

[57] ABSTRACT

The present invention is directed to a composition and method relating to the preparation of aspartyl peptides having the general formula:

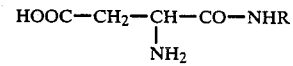

where the radical–NHR represents an amino acid or peptide group. In the method, a β-monoester of aspartic acid having the general formula:

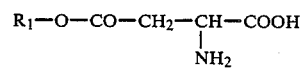

where R₁ represents a hydrocarbon-containing radical, is reacted with a β-dicarbonyl compound, preferably ethylacetoacetate to protect the aspartyl amino group and form an enamine. The enamine is then coupld to an amino acid or peptide, following which any protecting groups are removed to yield α-aspartyl peptides without any β-isomer. In its composition aspects, the present invention is directed to novel enamines resulting from reaction of the β-monoester of aspartic acid with a β-dicarbonyl compound.

33 Claims, No Drawings

METHOD RELATING TO PREPARATION OF ASPARTYL PEPTIDES

BACKGROUND OF THE INVENTION

1. Field of the Invention

The present invention is directed to a composition and method useful in preparing peptides and, more particularly, in the industrial synthesis of aspartyl peptides such as sweetening agents or polypeptide hormones.

2. Description of the Prior Art

It is well known that preparation of aspartyl peptides is especially difficult because aspartic acid has two non-identical acid functions. For example, the mixed anhydride of benzyloxycarbonyl aspartic acid, which is the accustomed intermediate for synthesis of these peptides, results in a mixture of $\alpha$ and $\beta$ aspartyl peptides, which is difficult to separate causing a reduction in the yield of the desired isomer.

To avoid formation of the non-desired isomer, certain methods in the literature have described use of aspartic acid derivatives with two protecting groups, one on the nitrogen and one on a selected acid function of the aspartic acid. For example, a combination of protecting groups in which the $\beta$-carboxyl group is converted to the $\beta$-benzyl ester, and the nitrogen is protected with benzyloxycarbonyl was described by Bryant, *Journal of the Chemical Society*, 1959, p. 3868 and by German Pat. No. 2.608.174. However, industrial peptide syntheses involving an aspartic acid intermediate having the foregoing protecting groups has proven impractical due to the length of time needed to prepare the intermediate, the cost of the raw materials (lithium hydroxide and benzyl chloroformate) and the problems arising from de-protection of the desired peptides. For example, hydrogenolysis of the two benzyl protections liberates toluene which impedes further hydrogenolysis by coating the catalyst.

DESCRIPTION OF THE INVENTION

In its method aspects, the present invention describes a new process to obtain aspartyl peptides with a satisfactory yield and without the inconvenience mentioned above.

As a composition of matter, the invention describes new derivatives of aspartic acid useful as intermediates in the industrial synthesis of aspartyl peptides.

In accordance with the method of the present invention, a $\beta$-monoester of aspartic acid having the general formula:

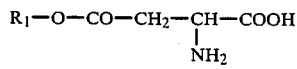

where $R_1$ represents a hydrocarbon-containing radical, is reacted with a $\beta$-dicarbonyl compound of formula:

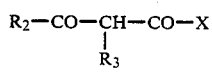

where the substituents $R_2$, $R_3$ and X have the meanings ascribed in the following three alternative cases:

Case 1: $R_2$ is a hydrocarbon-containing radical, a carbomethoxymethyl radical, or a carboethoxymethyl radical; $R_3$ is a hydrogen atom; and X is a hydrocarbon-containing radical or an alkoxy radical having the formula —$OR_4$ where $R_4$ is a hydrocarbon-containing radical or a radical having the formula —$NR_aR_b$ where $R_a$ and $R_b$ represents a hydrogen atom or a hydrocarbon-containing radical, or where $R_1$, $R_b$ and N constitutes a 5 or 6 member ring; or Case 2: $R_2$ and $R_3$ are bonded to one another and constitute a single alkyl chain portion of said $\beta$-dicarbonyl compound, said alkyl chain portion having the general formula —$(CH_2)_n$— where n is 3 or 4; and X has the meaning ascribed in (i) above; or Case 3: $R_2$ and X are bonded to one another and constitute a single three-carbon chain portion of said $\beta$-dicarbonyl compound; and $R_3$ is hydrogen.

The above reaction results in an enamine having the formula:

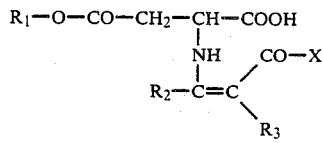

where $R_1$, $R_2$, $R_3$ and X have the definitions indicated above. The aspartyl enamine is then coupled with an amino acid or derivative thereof such as an amino acid ester or a peptide in a known manner involving conventional protection and deprotection steps to yield aspartyl peptides having the formula:

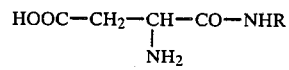

where —NHR represents an amino acid or peptide group.

In its composition aspects the present invention is directed to enamines derived from aspartic acid useful for the synthesis of aspartyl peptides, such enamines having the general formula:

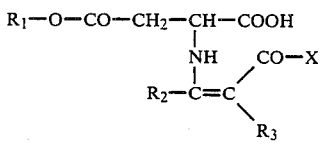

where $R_1$, $R_2$, $R_3$ and X have the meanings indicated above.

The expression "hydrocarbon-containing radical" used above signifies an alkyl radical with 1 to 5 carbon atoms (linear or branched) or a phenyl group either of the foregoing having optional methyl, halogen, or methoxy substitution, or a benzyl (or phenyl-1-ethyl) group having optional methyl, methoxy or nitro substitution.

In accordance with a preferred embodiment of the present method, the above-described $\beta$-monoester of aspartic acid and $\beta$-dicarbonyl compound are reacted in the presence of a secondary or tertiary amine to form the above-described enamine which can then be easily isolated as the enamine salt. The ability to readily isolate the enamine salt renders the enamine useful in different syntheses of aspartyl peptides. Of course, the aspartyl peptide synthesis of the present invention can be accomplished without isolating the enamine salt.

N-protection of amino acids to form enamine compounds with β-dicarbonyl derivatives although well known with respect to mono acids, is difficult for monoesters of diacids as indicated in literature references which discuss the β-benzyl ester of glutamic acid. See A. Balog, *Review of Rumanian Chemistry*, Vol. 15 (1970) p. 1375. Also, as indicated by R. Hirshmann et al., JACS 93; 2746 (1971), protection of aspartic acid via the β-methyl or β-benzyl monoester leads to the formation of both β- and α-aspartyl peptides, probably due to formation of the cylic intermediate causing interconversion of the α and β isomers. Such interconversion cannot be avoided and represents a serious drawback in the glutamic peptide synthesis. Given the greater instability of aspartic acid derivatives, as compared to glutamic derivatives, it is quite unexpected that the above-described aspartyl enamines could be prepared and used to obtain satisfactory yields in the industrial synthesis of aspartyl peptides without undergoing the abovementioned interconversion.

The optical isomers of aspartic acid result in formation of the D or L aspartyl enamines and the invention concerns any of these forms on their mixtures. Clearly, the salts obtained from an optically active amine will themselves be optically active, and this fact can be used to obtain aspartyl peptides of pre-determined optical activity.

The β-monoesters of aspartic acid used as starting reactants for this synthesis are generally well-known compounds, for example, the β-methyl, β-t-butyl, or β-benzyl ester of aspartic acid. The method which is ultimately chosen to de-protect the final aspartyl peptide will generally govern the selection of an appropriate monoester. For example, in the synthesis of L-α-aspartyl-L-methylphenylalaninate, the β-benzyl-L-aspartate is preferred to the β-methyl-L-aspartate because the β-methyl ester leads to a diester in which selective de-esterification is difficult to carry out.

Many different β-dicarbonyl compounds may be proposed for use as N-blocking agents in accordance with the present invention, i.e., β-diketones (e.g., acetylacetone, benzoylacetone, dibenzoylmethane, cyclohexanedione-1,3, or dimedone) or β-ketoesters (e.g., acetylacetic methyl ester, and ethyl-, butyl-, allyl-, benzyl- or α-methylbenzyl ester, cyclopentanone, cyclohexanone-2-methyl (or ethyl) carboxylate, pivaloyl acetate or methyl acetone discarboxylate or ethyl ester) or β-ketoamides (e.g., N,N-dimethylacetylacetamide, acetylacetanilide or methoxyacetylacetanilide). For practical use, β-ketoesters are preferred, in particular, ethylacetoacetate or methylacetoacetate.

The amines which may be utilized to facilitate the reaction between the β-monoester and the β-dicarbonyl compound are usually secondary amines with large groups substituted on the nitrogen atom, such as e.g., diisopropylamine, N-methylcyclohexylamine, dicyclohexylamine, N-tetramethyl-2,2,6,6 piperidine, N-methyl D- or L-α-methylbenzylamine, or also tertiary amines like triethylamine, tributylamine, N-methylmorpholine, N-methylpiperidine, N,N-dimethyl D- or L-α-methylbenzylamine. Dicyclohexylamine is generally preferred in isolating the enamines of the present invention formula in pure crystalline form.

Reaction of the β-monoester of aspartic acid with the β-dicarbonyl compound with the aid of the amine is carried out preferably in a solvent which may be an alcohol, such as methanol, ethanol, isopropanol or a butanol or an ether such as diethyl, diisopropyl, methyl tertiarybutyl, tetrahydrofuran or dioxane, or an ester such as ethyl acetate, isopropyl acetate, butoxy-2-ethyl acetate, or an aromatic hydrocarbon such as toluene, xylene, or an aliphatic hydrocarbon such as heptane or cyclohexane, or a ketone such as acetone, methylethylketone, or a halogenated solvent such as methylene chloride, chloroform, dichloro-1,2 ethane or chlorobenzene, or acetonitrile or a polar aprotic solvent such as dimethylformamide, dimethylacetamide, N-methylpyrrolidone, dimethylsulfoxide, hexamethylphosphotriamide ("HMPT") or any mixture of the above solvents. It is generally preferred to use a solvent where the reagents are soluble in the beginning, but where the end-product is an insoluble salt which can be isolated.

The above reaction can be initiated at ambient temperature but can be carried out at higher temperatures (up to 130° C.) to shorten reaction time, increase solubility of free agents, or to eliminate water by azeotropic distillation with the solvent. The elimination of water can also be accomplished by various chemicals compatible with the reaction, or for example, with 3 Angstrom molecular sieves, or other water-trapping agents.

The β-monoester and β-dicarbonyl compounds can be reacted in stoichiometric quantities, but it is preferred to use an excess of the amine and of the β-dicarbonyl compound in relation to the aspartic acid monoester. The enamines obtained can be isolated by filtration or centrifugation, after concentration of the reaction solvent, or after precipitation with the help of a second solvent. The enamine can also be obtained crude in solution for coupling with the amino acid or the peptide.

The aspartyl enamines of the present invention are most often solid, stable compounds and can be characterized by their melting point, by their infrared and ultraviolet absorption spectra and also by nuclear magnetic resonance, gas chromatography, and by high-pressure liquid chromatography.

The coupling of the aspartyl enamine with an amino acid, an amino acid ester, or a peptide can be carried out in accordance with conventional peptide coupling techniques for example by use of the dicyclohexylcarbodiimide method, the cyanomethyl ester method or, preferably, the mixed anhydride method.

In the first-mentioned coupling method, dicyclohexylcarbodiimide is added to a mixture of the aspartyl enamine of the present invention and a salt (e.g., the hydrochloride) of the aminoester to be acylated. The N-protected aspartyl peptide is obtained after elimination of the dicyclohexylurea by filtration.

In the second coupling method, involving use of cyanomethyl esters, the activated ester of the N-protected β-aspartic acid monoester is preliminarily prepared by reacting the aspartyl enamine with chloroacetonitrile, or preferably, tosyloxyacetonitrile, in an aprotic solvent. The resulting cyanomethyl ester is isolated and reacted under appropriate conditions with the aminoester to be acylated. See G. Wendlberger in Houben-Weyl "Methodon der Organischen Chemie" 1974 15/2 p. 8.

The mixed anhydride method is particularly simple to use: The aspartyl enamine of the present invention is treated with an acid chloride or a chloroformate in a convenient solvent. The resulting mixed anhydride is reacted with the amino ester and the product isolated as a base, or as a salt (e.g., hydrochloride) from which the base is liberated by additional use of one base equivalent. The N-protected peptide is obtained in solution.

Examples of suitable acid chlorides are acetyl chloride, pivaloyl chloride, or benzoyl chloride. Suitable chloroformates are, for example, methyl-, ethyl-, isopropyl- or isobutyl-, but preferably ethyl-chloroformate.

Coupling by the above methods is followed by deprotection of the N-protected peptide by simple hydrolysis of the enamine with an acid, such as hydrochloric acid. The α-aspartyl peptides thus obtained are very pure and without any β-isomer, indicating that interconversion between the α and β isomers often seen in conventional syntheses, does not occur in the method of the present invention. This unexpected result is very important and renders the present method far more useful than known methods.

The novel aspartyl enamines of the present invention are particularly useful intermediates in industrial peptide synthesis especially because of their great ease of preparation starting from common chemicals easily obtained, and also because of their great reactivity which is not usual for other intermediates used in conventional methods.

More particularly, it is possible to prepare in excellent yields peptides such as various angiotensins used in human and veterinary therapy, aspartame, pentagastrine, phyllomedusine, uperoleine, eledoisine or physalaemine. These known peptides can be prepared from the enamines of the present invention, in various steps, following well-known peptide syntheses techniques. For example the N-L-α-aspartyl-L-phenylalaninamide and the N-L-α-aspartyl-L-alanine, obtained directly from an enamine of the present invention Formula (III), are new intermediates for synthesis of pentagastrine and eledoisine respectively.

The following demonstrates use of this invention in more detail without limiting its scope.

EXAMPLE 1

Dicyclohexylamine Salt of N-(Carbethoxy-2 Methyl-1-Vinyl) β-L-Benzyl-Aspartate

A 4 liter reactor is loaded with 223 g of β-L-benzyl aspartate, 260 g ethylacetoacetate, 271 g dicyclohexylamine and 3 liters of dry toluene. After 48 hours of agitation at room temperature, the reactants are concentrated under vacuum to the smallest volume, following which 3 liters of heptane are added and the reactor agitated for 6 hours at about +10° C. The product is filtered and washed with 2 liters of heptane. After drying, 455 g of a white product is obtained with a chemical yield of 88%. Melting point 97° C. Equivalent molecular weight is 514 compared with a theoretical value of 516.

EXAMPLE 2

Dicyclohexylamine Salt From N-(Carbethoxy-2 Methyl-1-Vinyl) β-L-Tertiarybutyl Aspartate A 500 ml reactor is loaded with 18.9 g of β-L-tertiarybutyl aspartate, 26 g ethylacetoacetate, and 20 g dicyclohexylamine, plus 200 ml heptane. After 24 hours of agitation, the product is filtered, washed with 100 ml heptane, and dried. 7.7 g of white product are obtained with a yield of 16%. A second yield can be obtained by concentration of the filtrate. Melting point 124° C.

EXAMPLE 3

Diisopropylamine Salt of N-(Carbethoxy-2 Methyl-1-Vinyl) β-L-Benzyl Aspartate

A 500 ml reactor is loaded with 22.3 g of β-L-benzyl aspartate, 26 g ethylacetoacetate, and 11.3 g of diisopropylamine anhydride. After 72 hours of agitation at room temperature, the resulting oil crystallizes after a few hours of agitation with 300 ml of heptane. After filtration, washing and drying, a white powder is obtained with a yield of 77.6%. Melting point 100° C.

EXAMPLE 4

N-(Carbethoxy-2 Methyl-1-Vinyl) L-Benzyl Aspartate and α-Cyanomethyl Aspartate

A 500 ml reactor is loaded with 51.6 g of the compound obtained from Example 1, 216 g of tosyloxyacetonitrile, 250 ml acetone and 100 ml dimethylformamide. After 24 hours of agitation at room temperature 100 ml of water is added and the mixture cooled to about 0° C. The product is filtered and washed with water. After drying, the product is obtained in a yield of 65%. Melting point 104° C.

EXAMPLE 5

L-α-Aspartyl L-Methyl-Phenylalaninate

A one liter reactor is loaded with 51.6 g of the compound obtained from Example 1, 500 ml of isopropyl acetate and 70 ml of N,N-dimethylacetamide. The mixture is then cooled to about −20° C.

Over a period of one hour 10.1 ml of ethyl chloroformate is added slowly and the mixture agitated for about another hour at −20° C.

21.5 g of L-methyl-phenlalaninate hydrochloride is then added to the reactor, and 10.1 g of N-methylmorpholine is added slowly thereto over a period of about one hour, following which the temperature is gradually elevated to about +10° C. over a period of three hours.

300 ml of hydrochloric acid is then loaded into the reactor, and the mixture is agitated over a period of 12 hours at about 20° C. The organic phase is decanted and washed twice with normal hydrochloric acid in water, then the aqueous phases are united. At this stage, the total aqueous phase contains L-β-benzyl α-aspartyl L-phenyl alaninate methyl ester identifiable by its oxalate salt. (Melting point 170° C.)

6 g of activated carbon with 5% palladium is added and hydrogenation is carried out under 2 atmospheres for about 2 hours. The catalyst is filtered off and the pH raised to 5.3. After filtering, washing and drying, 14 g of product are obtained. (Yield 32%).

EXAMPLE 6

L-α-Aspartyl L-Methyl-Phenylalaninate (2nd Method)

A 500 ml reactor is loaded with 35 g of the compound obtained following Example 3, 17.25 g of the L-phenylalaninate methyl ester hydrochloride and 170 ml ethylacetoacetate. The suspension obtained is cooled to 0° C., followed by slow addition of 16.5 g of dicyclohexylcarbodiimide, with agitation, for 2 hours at 0° C. and 1 hour at 20° C.

Water is then added and the pH adjusted from 4 to 1 with hydrochloric acid. After 12 hours of agitation at room temperature, dicyclohexylurea is filtered off, and the organic phase is decanted and extracted with 50 ml hydrochloric acid normal in water. One gram of 5% palladium is added to the combined aqueous phases on activated carbon, followed by agitation for 3 hours under hydrogen atmosphere.

An HPLC assay shows that the solution contains about 23 g of the expected product (yield 35%.)

EXAMPLE 7

L-α-Aspartyl L-Methyl-Phenyl Alaninate (3rd Method)

A 1 liter reactor is loaded with 500 ml of isopropyl acetate and 51.6 g of the compound obtained from Example 1, followed by cooling to −20° C. 14.5 g pivaloyl chloride is added slowly over a period of 20 minutes and the reaction is maintained for another 30 minutes at −20° C.

21.6 g methyl L-phenyl alaninate hydrochloride is loaded into the reactor and then 10.1 g N-methyl morpholine is slowly added over a period of about 30 minutes. The reaction vessel is then agitated for one hour at −20° C., and another hour at +20° C.

After hydrolysis and hydrogenation using conventional methods, 4 g of methyl-L-α-aspartyl L-phenyl alaninate is isolated.

EXAMPLE 8

N-L-α-aspartyl-L-alanine

A 500 ml reactor is loaded with 25.8 g of the compound obtained according to Example 1, and 250 ml isopropyl acetate, followed by cooling to −20° C. 5 ml of ethyl chloroformate is added slowly over a 25 minute period followed by agitation for another 30 minutes at −20° C.

16.6 g of benzyl-L-alaninate tosylate is then quickly added, followed by addition of 5.1 g of N-methyl morpholine over a 15 minute period at −15° C. After 3 more hours of agitation between −15° and +20° C., 100 ml hydrochloric acid normal is added and the mixture is agitated for another 24 hours at room temperature.

After filtration and catalytic reduction under ordinary conditions 3.2 g of L-α-aspartyl L-alanine is obtained. Melting point 194°–196° C.

EXAMPLE 9

N-α-aspartyl L-phenylalaninamide

A 500 ml reactor is loaded with 25.8 g of the compound obtained according to Example 1, and 250 ml of ethyl acetate, followed by cooling to −25° C.

5 ml of ethyl chloroformate is added slowly over 30 minutes and the reaction vessel is agitated for another 30 minutes at −15° C. 10 g of phenylalaninamide hydrochloride is added, followed by 5.1 g of N-methyl morpholine added slowly over 20 minutes and at −15° C.

Further conventional treatment gives 6 g of N-α-aspartyl L-phenylalaninamide. Melting point 190° C.

We claim:

1. A method for preparing an α-aspartyl peptide having the general formula:

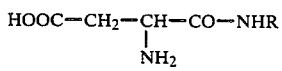

where —NHR represents an alanine, phenylalanine, or phenylalaninamide residue, the method comprising the steps of:

(a) reacting a β-monoester of aspartic acid having the general formula:

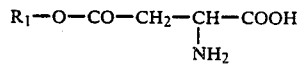

where $R_1$ denotes a linear or branched alkyl radical with 1 to 5 carbon atoms, a phenyl radical, a phenyl radical substituted by a methyl radical, a methoxy radical or a halogen atom, a benzyl radical, or a benzyl radical substituted by a methyl radical, a methoxy radical or a nitro group, with a β-dicarbonyl compound having the general formula:

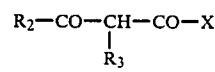

wherein:
(i) $R_2$ is a linear or branched alkyl radical with 1 to 5 carbon atoms, a phenyl radical, or a benzyl radical, a carbomethoxymethyl radical, or a carboethoxymethyl radical; $R_3$ is a hydrogen atom; and X is a linear or branched alkyl radical with 1 to 5 carbon atoms, a phenyl radical, or a benzyl radical, or an alkoxy radical having the formula —$OR_4$ where $R_4$ is a linear or branched alkyl radical with 1 to 5 carbon atoms, a phenyl radical, or a benzyl radical, or a radical having the formula —$NR_aR_b$ where $R_a$ and $R_b$ represent a hydrogen atom or a linear or brached alkyl radical with 1 to 5 carbon atoms, a phenyl radical, or a benzyl radical, or where $R_a$, $R_b$ and N constitute a 5- or 6-member ring; or
(ii) $R_2$ and $R_3$ are bonded to one another and constitute a single alkyl chain portion of said β-dicarbonyl compound, said alkyl chain portion having the general formula —$(CH_2)_n$— where n is 3 or 4; and X has the meaning ascribed in (i) above; or
(iii) $R_2$ and X are bonded to one another and constitute a single three-carbon chain portion of said β-dicarbonyl compound, said chain portion being unsubstituted or substituted by one or two methyl groups; and $R_3$ is hydrogen; in the presence of a secondary or tertiary amine to obtain an aspartyl enamine having the general formula:

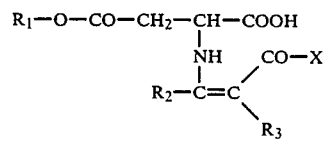

where $R_1$, $R_2$, $R_3$, and X have the meanings given in (i), (ii), and (iii) above; and
(b) reacting said aspartyl enamine with an amino acid or amino acid derivative selected from the group consisting of phenylalanine, alanine, phenylalaninamide, and salts or esters thereof to obtain an α-aspartyl peptide.

2. The method of claim 1 wherein the secondary or tertiary amine is selected from the group consisting of diisopropylamine, N-methylcyclohexylamine, dicyclohexylamine, N-tetramethyl-2,2,6,6 piperidine, N- methyl-D or L-α-methylbenzylamine, triethylamine, tributylamine, N-methylmorpholine, N-methylpiperidine, and N,N-dimethyl D- or L-α-methylbenzylamine.

3. The method of claim 1 or 2 wherein the step of reacting β-monoester of aspartic acid with the β-dicarbonyl compound is carried out in a solvent selected from the group consisting of an alcohol, a cyclic or linear ether, an ester, an aromatic hydrocarbon, an aliphatic hydrocarbon, a ketone, a halogenated solvent or a polar aprotic solvent or any mixture of the above solvents.

4. The method of claim 1 wherein the β-monoester of aspartic acid is selected from the group consisting of β-benzyl aspartate, β-methyl aspartate, and β-tertiarybutyl aspartate.

5. The method of claim 1 wherein the β-dicarbonyl compound is selected from the class consisting of methylacetoacetate, ethylacetoacetate, isopropylacetoacetate, and butylacetoacetate.

6. The method of claim 1 including removing N-protecting group from the α-aspartyl peptide.

7. The method of claim 6 wherein the protecting group is removed by hydrolysis.

8. A method for preparing an α-aspartyl peptide having the general formula:

$$HOOC-CH_2-CH(NH_2)-CO-NHR$$

where —NHR represents an alanine, phenylalanine, or phenylalaninamide residue, the method comprising the steps of:
(a) reacting a β-monoester of aspartic acid having the general formula:

$$R_1-O-CO-CH_2-CH(NH_2)-COOH$$

where $R_1$ denotes a linear or branched alkyl radical with 1 to 5 carbon atoms, a phenyl radical, a phenyl radical substituted by a methyl radical, a methoxy radical or a halogen atom, a benzyl radical, or a benzyl radical substituted by a methyl radical, a methoxy radical or a nitro group, with a β-dicarbonyl compound having the general formula:

$$R_2-CO-CH(R_3)-CO-X$$

wherein $R_2$ is a linear or branched alkyl radical with 1 to 5 carbon atoms, a phenyl radical, or a benzyl radical, a carbomethoxymethyl radical, or a carboethoxymethyl radical; $R_3$ is a hydrogen atom; and X is a linear or branched alkyl radical with 1 to 5 carbon atoms, a phenyl radical, or a benzyl radical, or an alkoxy radical having the formula $—OR_4$ where $R_4$ is a linear or branched alkyl radical with 1 to 5 carbon atoms, a phenyl radical, or a benzyl radical, or a radical having the formula $—NR_aR_b$ where $R_a$ and $R_b$ represent a hydrogen atom or a linear or branched alkyl radical with 1 to 5 carbon atoms, a phenyl radical, or a benzyl radical, or where $R_a$, $R_b$ and N constitute a 5- or 6-member ring; in the presence of a secondary or tertiary amine to obtain an aspartyl enamine having the general formula:

$$R_1-O-CO-CH_2-CH(NH-C(R_2)=C(R_3)-CO-X)-COOH$$

where $R_1$, $R_2$, $R_3$, and X have the meanings given above; and
(b) reacting said aspartyl enamine with an amino acid or amino acid derivative selected from the group consisting of phenylalanine, alanine, phenylalaninamide, and salts or esters thereof to obtain an α-aspartyl peptide.

9. The method of claim 8 wherein the secondary or tertiary amine is selected from the group consisting of diisopropylamine, N-methylcyclohexylamine, dicyclohexylamine, N-tetramethyl-2,2,6,6 piperidine, N-methyl-D or L-α-methylbenzylamine, triethylamine, tributylamine, N-methylmorpholine, N-methylpiperidine, and N,N-dimethyl D- or L-α-methylbenzylamine.

10. The method of claim 8 or 9 wherein the step of reacting the β-monoester of aspartic acid with the β-dicarbonyl compound is carried out in a solvent selected from the group consisting of an alcohol, a cyclic or linear ether, an ester, an aromatic hydrocarbon, an aliphatic hydrocarbon, a ketone, a halogenated solvent, or a polar aprotic solvent, or any mixture of the above solvents.

11. The method of claim 8 wherein the β-monoester of aspartic acid is selected from the group consisting of β-benzyl aspartate, β-methyl aspartate, and β-tertiarybutyl aspartate.

12. The method of claim 8 wherein the β-dicarbonyl compound is selected from the group consisting of methylacetoacetate, ethylacetoacetate, isopropylacetoacetate, and butylacetoacetate.

13. The method of claim 8 including removing N-protecting group from the α-aspartyl peptide.

14. The method of claim 13 wherein the N-protecting group is removed by hydrolysis.

15. A method for preparing an α-aspartyl peptide having the general formula:

$$HOOC-CH_2-CH(NH_2)-CO-NHR$$

where —NHR represents an alanine, phenylalanine, or phenylalaninamide residue, the method comprising the steps of:
(a) reacting a β-monoester of aspartic acid having the general formula:

$$R_1-O-CO-CH_2-CH(NH_2)-COOH$$

where $R_1$ denotes a linear or branched alkyl radical with 1 to 5 carbon atoms, a phenyl radical, a phenyl radical substituted by a methyl radical, a methoxy radical or a halogen atom, a benzyl radical, or a benzyl radical substituted by a methyl radical, a methoxy radical or a nitro group, with a β-dicarbonyl compound having the general formula:

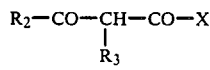

wherein $R_2$ and $R_3$ are bonded to one another and together constitute a single alkyl chain portion of said β-dicarbonyl compound, said alkyl chain portion having the general formula $-(CH_2)_n-$ where n is 3 or 4; and X is a linear or branched alkyl radical with 1 to 5 carbon atoms, a phenyl radical, or a benzyl radical, or an alkoxy radical having the formula $-OR_4$ where $R_4$ is a linear or branched alkyl radical with 1 to 5 carbon atoms, a phenyl radical, or a benzyl radical, or a radical having the formula $-NR_aR_b$ where $R_a$ and $R_b$ represent a hydrogen atom or a linear or brached alkyl radical with 1 to 5 carbon atoms, a phenyl radical, or a benzyl radical, or where $R_a$, $R_b$ and N constitute a 5- or 6-member ring, in the presence of a secondary or tertiary amine to obtain an aspartyl enamine having the general formula:

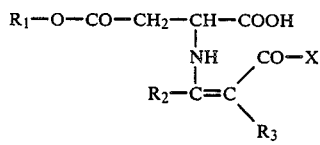

where $R_1$, $R_2$, $R_3$, and X have the meanings given above; and (b) reacting said aspartyl enamine with an amino acid or amino acid derivative selected from the group consisting of phenylalanine, alanine, phenylalaninamide, and salts or esters thereof to obtain an α-aspartyl peptide.

16. The method of claim 15 wherein the secondary or tertiary amine is selected from the group consisting of diisopropylamine, N-methylcyclohexylamine, dicyclohexylamine, N-tetramethyl-2,2,6,6 piperidine, N-methyl-D or L-α-methylbenzylamine, triethylamine, tributylamine, N-methylmorpholine, N-methylpiperidine, and N,N-dimethyl D-or L-α-methylbenzylamine.

17. The method of claim 15 or 16 wherein the step of reacting the β-monoester of aspartic acid with the β-dicarbonyl compound is carried out in a solvent selected from the group consisting of an alcohol, a cyclic or linear ether, an ester, an aromatic hydrocarbon, an aliphatic hydrocarbon, a ketone, a halogenated solvent, or a polar aprotic solvent, or any mixture of the above solvents.

18. The method of claim 15 wherein the β-monoester of aspartic acid is selected from the group consisting of β-benzyl aspartate, β-methyl aspartate, and β-tertiarybutyl aspartate.

19. The method of claim 15 wherein the β-dicarbonyl compound is selected from the group consisting of methylacetoacetate, ethylacetoacetate, isopropylacetoacetate, and butylacetoacetate.

20. The method of claim 15 including removing N-protecting group from the α-aspartyl peptide.

21. The method of claim 20 wherein the N-protecting group is removed by hydrolysis.

22. A method for preparing an α-aspartyl peptide having the general formula:

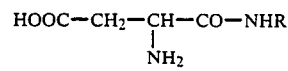

where $-NHR$ represents an alanine, phenylalanine, or phenylalaninamide residue, the method comprising the steps of:

(a) reacting a β-monoester of aspartic acid having the general formula:

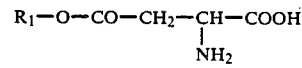

where $R_1$ denotes a linear or branched alkyl radical with 1 to 5 carbon atoms, a phenyl radical, a phenyl radical substituted by a methyl radical, a methoxy radical or a halogen atom, a benzyl radical, or a benzyl radical substituted by a methyl radical, a methoxy radical or a nitro group, with a β-dicarbonyl compound having the general formula:

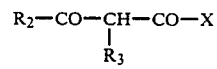

wherein $R_2$ and X are bonded to one another and together constitute a single three-carbon chain portion of said β-dicarbonyl compound, said chain portion being unsubstituted or substituted by one or two methyl groups; and $R_3$ is hydrogen, in the presence of a secondary or tertiary amine to obtain as aspartyl enamine having the general formula:

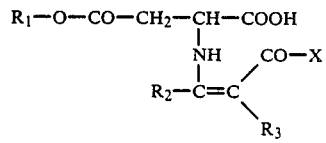

where $R_1$, $R_2$, $R_3$, and X have the meanings given above; and (b) reacting said aspartyl enamine with an amino acid or amino acid derivative selected from the group consisting of phenylalanine, alaline, phenylalaninamide, and salts or esters thereof to obtain an α-aspartyl peptide.

23. The method of claim 22 wherein the secondary or tertiary amine is selected from the group consisting of diisopropylamine, N-methylcyclohexylamine, dicyclohexylamine, N-tetramethyl-2,2,6,6 piperidine, N-methyl-D or L-α-methylbenzylamine, triethylamine, tributylamine, N-methylmorpholine, N-methylpiperidine, and N,N-dimethyl D-or L-α-methylbenzylamine.

24. The method of claim 22 or 23 wherein the step of reacting the β-monoester of aspartic acid with the β-dicarbonyl compound is carried out in a solvent selected from the group consisting of an alcohol, a cyclic or linear ether, an ester, an aromatic hydrocarbon, an aliphatic hydrocarbon, a ketone, a halogenated solvent, or a polar aprotic solvent, or any mixture of the above solvents.

25. The method of claim 22 wherein the β-monoester of aspartic acid is selected from the group consisting of β-benzyl aspartate, β-methyl aspartate, and β-tertiarybutyl aspartate.

26. The method of claim 22 wherein the β-dicarbonyl compound is selected from the group consisting of methylacetoacetate, ethylacetoacetate, isopropylacetoacetate, and butylacetoacetate.

27. The method of claim 22 including removing N-protecting group from the α-aspartyl peptide.

28. The method of claim 27 wherein the N-protecting group is removed by hydrolysis.

29. A method for preparing an α-aspartyl peptide having the general formula:

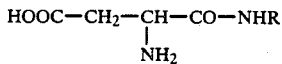

where —NHR represents an alanine, phenylalanine, or phenylalaninamide residue, the method comprising the steps of:

(a) reacting a β-monoester of aspartic acid having the general formula:

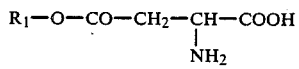

where $R_1$ denotes a linear or branched alkyl radical with 1 to 5 carbon atoms, a phenyl radical, a phenyl radical substituted by a methyl radical, a methoxy radical or a halogen atom, a benzyl radical, or a benzyl radical substituted by a methyl radical, a methoxy radical or a nitro group, with a β-dicarbonyl compound having the general formula:

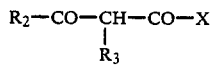

wherein:

(i) $R_2$ is a linear or branched alkyl radical with 1 to 5 carbon atoms, a phenyl radical, or a benzyl radical, a carbomethoxymethyl radical, or a carboethoxymethyl radical; $R_3$ is a hydrogen atom; and X is a linear or branched alkyl radical with 1 to 5 carbon atoms, a phenyl radical, or a benzyl radical, or an alkoxy radical having the formula —$OR_4$ where $R_4$ is a linear or branched alkyl radical with 1 to 5 carbon atoms, a phenyl radical, or a benzyl radical, or a radical having the formula —$NR_aR_b$ where $R_a$ and $R_b$ represent a hydrogen atom or a linear or branched alkyl radical with 1 to 5 carbon atoms, a phenyl radical, or a benzyl radical; or (ii) $R_2$ and $R_3$ are bonded to one another and constitute a single alkyl chain portion of said β-dicarbonyl compound, said alkyl chain portion having the general formula —$(CH_2)_n$— where n is 3 or 4; and X has the meaning ascribed in (i) above; or (iii) $R_2$ and X are bonded to one another and constitute a single three-carbon chain portion of said β-dicarbonyl compound, said chain portion being unsubstituted or substituted by one or two methyl groups; and $R_3$ is hydrogen; in the presence of a secondary or tertiary amine to obtain an aspartyl enamine having the general formula:

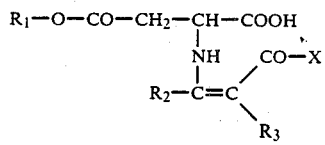

where $R_1$, $R_2$, $R_3$, and X have the meanings given in (i), (ii), and (iii) above; and (b) reacting said aspartyl enamine with an amino acid or amino acid derivative selected from the group consisting of phenylalanine, alanine, phenylalaninamide, and salts or esters thereof to obtain an α-aspartyl peptide.

30. A method for preparing an α-aspartyl peptide having the general formula:

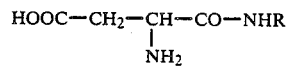

where —NHR represents an alanine, phenylalanine, or phenylalaninamide residue, the method comprising the steps of:

(a) reacting a β-monoester of aspartic acid having the general formula:

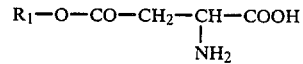

where $R_1$ denotes a linear or branched alkyl radical with 1 to 5 carbon atoms, a phenyl radical, a phenyl radical substituted by a methyl radical, a methoxy radical or a halogen atom, a benzyl radical, or a benzyl radical substituted by a methyl radical, a methoxy radical or a nitro group, with a β-dicarbonyl compound having the general formula:

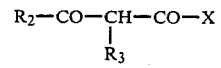

wherein $R_2$ is a linear or branched alkyl radical with 1 to 5 carbon atoms, a phenyl radical, or a benzyl radical, a carbomethoxymethyl radical, or a carboethoxymethyl radical; $R_3$ is a hydrogen atom; and X is a linear or branched alkyl radical with 1 to 5 carbon atoms, a phenyl radical, or a benzyl radical, or an alkoxy radical having the formula —$OR_4$ where $R_4$ is a linear or branched alkyl radical with 1 to 5 carbon atoms, a phenyl radical, or a benzyl radical, or a radical having the formula —$NR_aR_b$ where $R_a$ and $R_b$ represent a hydrogen atom or a linear or branched alkyl radical with 1 to 5 carbon atoms, a phenyl radical, or a benzyl radical, in the presence of a secondary or tertiary amine to obtain an aspartyl enamine having the general formula:

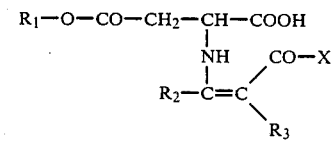

where $R_1$, $R_2$, $R_3$, and X have the meanings given above; and (b) reacting said aspartyl enamine with an amino acid or amino acid derivative selected from the group consisting of phenylalanine, alanine, phenylalaninamide, and salts or esters thereof to obtain an α-aspartyl peptide.

31. The method of claim 10 wherein said polar aprotic solvent is selected from the group consisting of dimethyl formamide, dimethylacetamide, N-methylpyrrolidone, dimethylsulfoxide, and hexamethylphosphotriamide.

32. The method of claim 17, wherein said polar aprotic solvent is selected from the group consisting of dimethyl formamide, dimethylacetamide, N-methylpyrrolidone, dimethylsulfoxide, and hexamethylphosphotriamide.

33. The method of claim 24, wherein said polar aprotic solvent is selected from the group consisting of dimethyl formamide, dimethylacetamide, N-methylpyrrolidone, dimethylsulfoxide, and hexamethylphosphotriamide.

* * * * *